(12) United States Patent
Greis et al.

(10) Patent No.: US 10,822,636 B2
(45) Date of Patent: Nov. 3, 2020

(54) METHOD FOR DETERMINING FIBRINOGEN AND AUTOMATIC ANALYZER

(71) Applicant: Siemens Healthcare Diagnostics Products GmbH, Marburg (DE)

(72) Inventors: Dirk Greis, Burgwald (DE); Norbert Zander, Marburg (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 173 days.

(21) Appl. No.: 16/080,291

(22) PCT Filed: Mar. 28, 2017

(86) PCT No.: PCT/EP2017/057239
§ 371 (c)(1),
(2) Date: Aug. 27, 2018

(87) PCT Pub. No.: WO2017/167706
PCT Pub. Date: Oct. 5, 2017

(65) Prior Publication Data
US 2019/0330677 A1    Oct. 31, 2019

(30) Foreign Application Priority Data

Mar. 31, 2016   (EP) .................................... 16163255

(51) Int. Cl.
*C12Q 1/56* (2006.01)
*B01L 3/02* (2006.01)
*G01N 21/59* (2006.01)
*G01N 35/00* (2006.01)
*G01N 35/10* (2006.01)

(52) U.S. Cl.
CPC ............... *C12Q 1/56* (2013.01); *B01L 3/021* (2013.01); *G01N 21/59* (2013.01); *G01N 35/00584* (2013.01); *G01N 35/10* (2013.01); *G01N 35/1002* (2013.01); *B01L 2200/14* (2013.01); *B01L 2200/16* (2013.01); *B01L 2300/0636* (2013.01)

(58) Field of Classification Search
CPC ............... G01N 33/86; G01N 2333/75; G01N 2800/32; G01N 2021/825; G01N 21/82; G01N 2800/323; G01N 2800/324; G01N 2800/50; G01N 33/577; G01N 21/272; G01N 21/59; G01N 2333/7454; G01N 2333/94; G01N 33/4905; G01N 33/582; G01N 35/00584; G01N 35/10; G01N 35/1002; A61P 3/06; A61P 7/02; A61P 9/00; A61P 9/10; A61P 9/12; C12Q 1/56; C12Q 1/6883; C12Q 2600/156; C12Q 2600/172; C12Q 1/00; C12Q 2525/301; C12Q 2563/125; C12Q 1/6816; C12Q 1/6897; C12Q 1/682; C12Q 1/6823; C12Q 1/6825; A61K 38/00; A61K 47/542; A61K 47/60; A61K 47/64; A61K 49/0032; A61K 49/0056; A61K 49/14; A61K 49/1821; B01L 2200/14; B01L 2200/16; B01L 2300/0636; B01L 3/021; B60K 2006/381; B60K 6/38; B60K 6/387; B60K 6/445; B60T 13/586; B60T 1/005; B60T 1/10; B60T 2260/04; B60T 2270/60; B60T 8/17; B60W 20/40; B60W 30/18136; B60Y 2200/92; B60Y 2400/42; C07K 17/14; C07K 7/08; F16D 61/00; F16H 63/34; F16H 63/3425; G06F 19/3481; Y10S 903/914; Y10S 903/947
See application file for complete search history.

(56) References Cited

U.S. PATENT DOCUMENTS

| | | | | |
|---|---|---|---|---|
| 5,197,017 A | * | 3/1993 | Carroll | .................. G01N 33/86 |
| | | | | 422/73 |
| 2010/0235103 A1 | * | 9/2010 | Carroll | .................. G01N 21/82 |
| | | | | 702/19 |
| 2011/0014640 A1 | | 1/2011 | Yamamoto et al. | |
| 2017/0363650 A1 | * | 12/2017 | Van Ooijen | ........ A61K 49/0032 |

FOREIGN PATENT DOCUMENTS

| | | |
|---|---|---|
| CA | 1062501 A | 9/1979 |
| CN | 101983338 | 3/2011 |
| EP | 0699909 A2 | 3/1996 |
| EP | 2546637 A1 | 1/2013 |

OTHER PUBLICATIONS

Poon et al, "Quantitative reagent-free detection of fibrinogen levels in human blood plasma using Raman spectroscopy", Analyst, 2012, 137, 1807-14 www.rsc.org/analyst. (Year: 2012).*
Thomas, L., Labor and Diagnose, 7. Auflage, TH-Books Verlagsgesellschaft mbH, Frankfurt/Main, 2008, Kapitel 16.15.2; Equivalent to Chapter 17.15.2 in 1. English Edition, 1998, pp. 609-610.
Halbmayer Walter-Michael et al: "Comparison of a new automated kinetically determined fibrinogen assay with the 3 most used fibrinogen assays (functional, derived and nephelometric) in Austrian laboratories in several clinical populations and healthy controls"; Haemostasis, Bd. 25, Nr. 3, pp. 114-123, XP889198341; ISSN: 8381-8147; 1995.
A. Clauss, Gerinnungsphysiologische Schnellmethode zur Bestimmung des Fibrinogens. 1957, Acta haemat. 17: 237-246.
(Continued)

*Primary Examiner* — Deborah K Ware
(74) *Attorney, Agent, or Firm* — Dugan & Dugan, PC (57) ABSTRACT

The invention relates to the field of blood clotting diagnosis and relates to a kinetic method for determining the fibrinogen concentration in a human plasma sample according to the Clauss method.

7 Claims, 4 Drawing Sheets

(56) References Cited

International Search Report and Written Opinion (English Version) of International Application No. PCT/EP2017/057239 dated May 29, 2017.
International Search Report and Written Opinion (German Version) of International Application No. PCT/EP2017/057239 dated May 29, 2017.
European Search Report of European Application No. 16163255.9-1408 dated Jun. 10, 2016.
"Pharmokinetics", Zhejiang University Press ("Determination of Enzyme Kinetic Parameters") edited by Zeng Su; Dec. 31, 2008.
Chinese Office Action of corresponding Chinese Application No. 2017800033083 dated Aug. 23, 2019.
Jespersen J. et al; "A Study of the Conditions and Accuracy of the Thrombin Time Assay of Plasma Fibrinogen"; Acta Haematologica 67: 2-7; 1982.
Chinese Search Report of Chinese Application No. 2017800033083 dated Nov. 6, 2018.

* cited by examiner

METHOD FOR DETERMINING FIBRINOGEN AND AUTOMATIC ANALYZER

CROSS REFERENCE TO RELATED APPLICATIONS

This is a 371 of PCT/EP2017/057239, filed Mar. 28, 2017, which claims priority to European Patent Application No. EP 16163255.9, filed Mar. 31, 2016, both of which are hereby incorporated by reference herein in their entireties for all purposes.

FIELD

The present invention lies in the field of blood-clotting diagnostics and relates to a method for determining the concentration of fibrinogen in a human plasma sample according to the Clauss method.

BACKGROUND

Fibrinogen is the water-soluble precursor of fibrin, which forms the matrix for wound closure. The clotting protease thrombin (factor IIa) cleaves fibrinogen and, in this way, activates the formation of fibrin, i.e., clot formation. Lowered fibrinogen levels are associated with a susceptibility to bleeding. Acutely elevated fibrinogen levels are frequently found in the case of inflammations, postoperatively and in other situations. Long-term elevated fibrinogen levels are considered to be a risk indicator for thrombotic disorders.

In the prior art, a range of different methods for determining the concentration of fibrinogen are known.

CA 1062501 describes a fibrinogen determination method based on the measurement of the thrombin time, it being known that the thrombin time does not allow a precise determination of the concentration of fibrinogen, because other factors in addition to fibrinogen, such as, for example, anticoagulants such as heparin or direct thrombin inhibitors or else the presence of fibrin cleavage products or fibrinogen cleavage products, may influence the thrombin time, and the thrombin time generally only works in the case of severe fibrinogen deficiencies. In a thrombin time method, an undiluted plasma sample is usually mixed with a comparatively low amount of thrombin and the formation of fibrin, i.e., the absorbance change of the reaction mix, is measured photometrically followed by determination of the clotting time. However, according to CA 1062501, clotting time is not determined; instead, what is determined is the maximum of the first derivative of the reaction curve or, in other words, the maximum absorbance change of the reaction curve. It was found that the maximum absorbance change correlates linearly with the concentration of fibrinogen, meaning that the latter can be determined with the aid of a calibration curve which has been prepared from an assignment of known fibrinogen concentrations and maximum absorbance changes.

A method for determining the concentration of fibrinogen that is substantially more precise and frequently used is the so-called Clauss method (Clauss, A., Gerinnungsphysiologische Schnellmethode zur Bestimmung des Fibrinogens [Rapid clotting-physiology method for determining fibrinogen], 1957, Acta haemat. 17: 237-246). The test is a variant of the thrombin time, in which a plasma sample is mixed with thrombin and the clotting time is determined. In the Clauss method, a comparatively low concentration of fibrinogen is combined with a comparatively high, standardized concentration of thrombin in the reaction mix, the result being that the rate of fibrin formation practically exclusively correlates with the concentration of fibrinogen. The comparatively low concentration of fibrinogen in the reaction mix is usually produced through the use of prediluted plasma samples.

In the reaction mix, the formation of fibrin, i.e., clot formation, is then determined photometrically. Owing to the formation of fibrin, the reaction mix increases in turbidity, meaning that the formation of fibrin can be quantitatively measured by means of an absorption measurement.

Usually, the clotting time of the sample is then determined. The clotting time of the sample behaves proportionally in relation to the amount of fibrinogen. The clotting time of a sample is the time from the time of addition of thrombin to the sample up to the time of measurement of an identifiable formation of fibrin, i.e., turbidity of the reaction mix. In this connection, the "identifiable formation of fibrin" can be defined as a test-specific and instrument-specific threshold which—when it is exceeded—indicates the clotting time. Alternatively, the "identifiable formation of fibrin" can, proceeding from the difference in signal before the start of and after completion of the clotting reaction, be defined as a test-specific and instrument-specific percentage signal-difference value which—when it has been reached—indicates the clotting time. The reaction kinetics of the formation of fibrin in a Clauss test differ considerably from the reaction kinetics of the formation of fibrin in a thrombin time test. In the case of the Clauss test, the formation of fibrin starts, depending on the concentration of fibrinogen, as early as 3 seconds after addition of the thrombin reagent, i.e., substantially earlier than in the case of the thrombin time test, in which the formation of fibrin starts after 10 seconds at the earliest. In addition, the rate of fibrin formation in the case of the Clauss test is, at least in samples of comparatively high concentration, higher than in the case of the thrombin time test. The reaction curves for samples of high fibrinogen concentration in the case of the Clauss test are, in comparison with the thrombin time test, therefore distinguished by a short lag phase, a steep rise and a relatively rapidly reached plateau phase. The reaction curves for samples of low fibrinogen concentration in the case of the Clauss test exhibit, in comparison with the thrombin time test, likewise a short lag phase, a gentle rise and a plateau phase which is so late that it usually occurs only after completion of the measurement. By contrast, in the case of the thrombin time, the plateau phase is distinctly more weakly pronounced or it is even completely omitted.

What is problematic is that, owing to the relatively high dilution of the plasma samples in the Clauss test, only relatively low signal strengths are achieved, which can lead to imprecise measurement results as a result of the low signal-to-noise ratio in optical systems and simply as a result of minor disturbances, such as, for example, gas bubbles in the reaction mix, which can arise through the use of cooled reagents.

To avoid these problems, use is made in the prior art of uncooled reagents, and/or kaolin is added as signal-boosting additive reagent.

The use of uncooled reagents has the disadvantage that the reagents have a reduced stability and should be used up as quickly as possible. In addition, cooled storage positions for reagent containers are exclusively provided in modern analyzers in many cases, meaning that it is not readily possible to provide uncooled reagent. The use of signal-boosting additive reagents is likewise undesirable, firstly for economic reasons and secondly because the additionally required pipetting step extends the execution of the test.

Furthermore, the clot which forms can, particularly in the case of low plasma levels of fibrinogen, agglomerate and float around in the reaction mix as a "fibrin-kaolin bubble".

What is further problematic is that, when determining the clotting time of a sample in the Clauss test, the measurement should ideally be started immediately after the addition of the thrombin to the sample. However, in practice, when the procedure is automated on analyzers, a short period of time (several seconds) elapses between the addition of the thrombin reagent to the reaction vessel and the placement of the reaction vessel in the measurement position. However, in the case of very high plasma levels of fibrinogen, what can already happen during this short time is a start to the reaction and thus a rise in signal. In this case, a traditional determination of the clotting time is difficult, since the start value must be known for the "identifiable formation of fibrin", either via a test-specific and instrument-specific threshold or, alternatively, via the percentage signal difference based on the start and completion of the clotting reaction.

SUMMARY

It is thus an object of the invention to modify the Clauss method for determining the concentration of fibrinogen in a human plasma sample in such a way that it is possible to carry out an automatic execution with high precision and that it is possible to dispense with the use of uncooled reagents and the use of signal-boosting additive reagents, such as, for example, kaolin.

The object is achieved by no longer determining the hitherto customary clotting time of the sample, but by measuring the reaction kinetics of the formation of fibrin and by using the reaction rate to determine the concentration of fibrinogen.

The present application thus provides a method for determining the concentration of fibrinogen in a human plasma sample according to the Clauss method, the method comprising the steps:
  providing a reaction mix containing the plasma sample and thrombin,
  measuring the absorbance values of the reaction mixture over time,
  preparing a reaction curve from the measured absorbance values over time,
  ascertaining the maximum absorbance change by means of a regression method, and
  determining the concentration of fibrinogen with the aid of a calibration curve which has been prepared from an assignment of known fibrinogen concentrations and maximum absorbance changes.

The mixing ratio of plasma sample and thrombin units to provide a reaction mix according to the Clauss method, i.e., the combination of a comparatively low concentration of fibrinogen (from the sample) with a comparatively high concentration of thrombin, with the result that the rate of fibrin formation practically exclusively correlates with the concentration of fibrinogen, is sufficiently known to a person skilled in the art (see also Thomas, L., Labor and Diagnose [Laboratory and diagnosis], 7th edition, TH-Books Verlagsgesellschaft mbH, Frankfurt/Main, 2008, chapter 16.15.2).

Preferably, the reaction mix contains to this end about 0.03 to 0.4 mg/mL fibrinogen and about 25 to 40 IU/mL thrombin. These concentrations can, for example, be obtained by mixing in a ratio of 2+1 an about 1:10 dilution of a plasma sample under investigation in a buffer and a buffered thrombin reagent having a concentration of about 100 IU/mL thrombin. This means that fibrinogen concentrations from about 0.5 g/L to 6.0 g/L can be determined. By changing the predilution of the sample, it is possible to measure the entire physiologically occurring range of fibrinogen in human plasma.

The measurement of the absorbance values of the reaction mixture over time can be done photometrically, i.e., by means of the measurement of the light attenuation of a light beam transmitted through the reaction mix, or nephelometrically, i.e., by means of the measurement of scattered light portions of a light beam transmitted through the reaction mix. Ideally, the measurement is started immediately after the addition of the thrombin to the sample, and the measurement of the absorbance values is carried out continuously until the completion of the formation of fibrin. However, in practice, when the procedure is automated on analyzers, a short period of time (several seconds) elapses between the addition of the thrombin reagent to the reaction vessel with subsequent mixing and the placement of the reaction vessel in the measurement position.

It has been found that the method according to the invention is especially suitable for test protocols in which an immediate measurement of the absorbance values is not possible, for example because the reaction mix must first be transported to the measurement station. In a specific embodiment in which the provision of a reaction mix comprises the addition of thrombin to the plasma sample, there is a period of time from 0.5 to 5 seconds, preferably from 3 to 4 seconds, between the time of addition of thrombin to the plasma sample and the start of the measurement of the absorbance values of the reaction mixture.

The regression method used to ascertain the maximum absorbance change is a kinetic evaluation method, which is known to a person skilled in the art and in which, depending on a gradient of the reaction curve that is roughly ascertained in a first evaluation step, an individual and optimized regression interval is determined in a second evaluation step for the calculation of the maximum reaction rate, i.e., the maximum absorbance change.

Preferably, the regression method comprises the following steps:
  a first step in which a first, provisional maximum absorbance change in the reaction curve is determined using a predetermined first regression interval,
  a second step in which a second regression interval is determined on the basis of the first, provisional maximum absorbance change that is determined and on the basis of predetermined parameters, and
  a third step in which the maximum absorbance change is determined using the second regression interval.

Thus, preferably, within a defined test-specific and instrument-specific evaluation range starting from the first measurement value (which is as close as possible to the time of addition of thrombin), the gradient (=reaction rate or absorbance change) is first calculated over a test-specific and instrument-specific regression interval by regression according to the method of least squares. This calculation is repeated multiple times by using the second measurement value, third measurement value, fourth measurement value, etc., as starting point of the regression interval.

The provisional maximum gradient (rough gradient) that is thus ascertained is used to calculate the final regression interval via a power function with empirically predetermined parameters factor and exponent. Via a negative exponent, the desired effect that the regression interval becomes shorter with growing gradient is achieved. In principle, the calculation of the final regression interval can, however, also be done via a different equation or be gathered from a table deposited in the software.

Using the final regression interval that is calculated, the final maximum gradient is ascertained as already described above, again by regression according to the method of least squares starting from the first measurement value. This calculation is repeated multiple times by using the second measurement value, third measurement value, fourth measurement value, etc., as starting point of the regression interval.

It has been found that, by using this two-step regression method to ascertain the maximum gradient of Clauss test reaction kinetics, it is possible to precisely determine the concentration of fibrinogen in samples of high fibrinogen concentration as well as in samples of low fibrinogen concentration, even if there are disturbances in the reaction kinetics, such as, for example, gas bubbles in the reaction mix, which overlay the actual measurement signal and thus contain a "false" maximum gradient.

The determination of the concentration of fibrinogen in the sample is, then, done with the aid of a calibration curve which has been prepared from an assignment of known fibrinogen concentrations and maximum gradient (=maximum absorbance change).

The present invention further provides an automatic analyzer comprising at least one pipetting device, a photometric or nephelometric measurement station and a data processing unit, characterized in that the analyzer further comprises a controller configured in such a way that it controls a method for determining the concentration of fibrinogen according to the Clauss method, comprising the following steps:
provided a reaction mix containing a plasma sample and thrombin,
measuring the absorbance values of the reaction mixture over time,
preparing a reaction curve from the measured absorbance values over time,
ascertaining the maximum absorbance change by means of a regression method, and
determining the concentration of fibrinogen with the aid of a calibration curve which has been prepared from an assignment of known fibrinogen concentrations and maximum absorbance changes.

Such automatic analyzers are used routinely in analytical chemistry, forensics, microbiology and clinical diagnostics in order to analyze a multiplicity of samples in a multiplicity of test methods in a rapid, exact and reproducible manner.

An analyzer according to the invention comprising a controller configured in such a way that it controls the performance of a Clauss test in combination with the above-described kinetic evaluation has the advantage that said analyzer allows a precise fibrinogen determination to be performed, there being no need to provide uncooled storage positions for the reagents used for the provision of the reaction mix, for the thrombin reagent in particular.

The provision of a reaction mix containing the plasma sample and thrombin in the automatic analyzer is typically carried out with the aid of one or more automatic pipetting devices.

The measurement of the absorbance values of the reaction mixture over time is typically done in the photometric or nephelometric measurement station.

A "photometric measurement station" is to be understood to mean a measurement unit which comprises at least one light source and at least one light detector and which is designed in such a way that it allows the measurement of the absorbance of light of a certain wavelength in a sample. Typically, the wavelength of the light emitted by the light source is selected such that it is attenuated (absorbed, reflected or scattered) by a substance to be detected in the sample, in this case fibrin.

A "nephelometric measurement station" is to be understood to mean a measurement unit which comprises at least one light source and at least one light detector and which is designed in such a way that it allows the measurement of the absorbance of light in a sample. Typically, the arrangement of light source and light detector is selected such that it is possible to measure the scattered light which is scattered by macromolecules to be detected in the sample, for example by particle aggregates arising in a reaction mix as a result of an analyte-dependent reaction, or, in this case, by fibrin.

For the determination of the concentration of fibrinogen with the aid of a calibration curve, the corresponding assignment of known fibrinogen concentrations and maximum absorbance changes is stored preferably in the data processing unit. In the data processing unit, the ascertainment of the concentration of fibrinogen is then also carried out by reading of the fibrinogen concentration corresponding to the ascertained maximum absorbance change of the reaction mix.

One embodiment of an automatic analyzer according to the invention further comprises a first accommodation position for reaction vessels, which position is intended for the provision of reaction mixes, and a second accommodation position for reaction vessels, which position is assigned to the measurement station, and a device for transporting a reaction vessel from the first accommodation position to the second, wherein the controller is further configured in such a way that it further controls the following steps:
providing in the first accommodation position for reaction vessels a reaction vessel containing the reaction mix by addition of thrombin to a plasma sample present in the reaction vessel,
transporting the reaction vessel from the first accommodation position to the second, and then
measuring the absorbance values of the reaction mixture over time,
wherein there is a period of time from 0.5 to 5 seconds, preferably from 3 to 4 seconds, between the time of addition of thrombin to the plasma sample and the start of the measurement of the absorbance values of the reaction mixture.

The reaction vessel is preferably a transparent, tubular cuvette made of plastic or glass.

An "accommodation position" for a reaction vessel means a site intended for the placement of a reaction vessel. In many cases, this is a structurally adapted accommodation device which allows the liquid container to be stored stably, such as, for example, adaptors into which a specifically designed reaction vessel can be inserted in a form-fitting manner. In many cases, an accommodation position is situated on movable accommodation apparatuses, such as, for example, rotatable cuvette plates or rings, which have a multiplicity of accommodation positions. Accommodation positions assigned to a measurement station are designed and arranged in such a way that the measurement of a reaction mixture present in a reaction vessel is possible therein.

In many cases, grippers attached to a transfer arm movable in a horizontal and vertical manner are provided for the transport of reaction vessels between two accommodation positions situated on spatially separate accommodation apparatuses, for example, between a first accommodation position to which a pipetting device has access and in which reaction mixes can be provided and incubated and a second accommodation position in which the measurement of the reaction mixtures takes place.

BRIEF DESCRIPTION OF THE DRAWINGS

The invention will be elucidated below with reference to a drawing.

Here.

DETAILED DESCRIPTION

Figure 1:
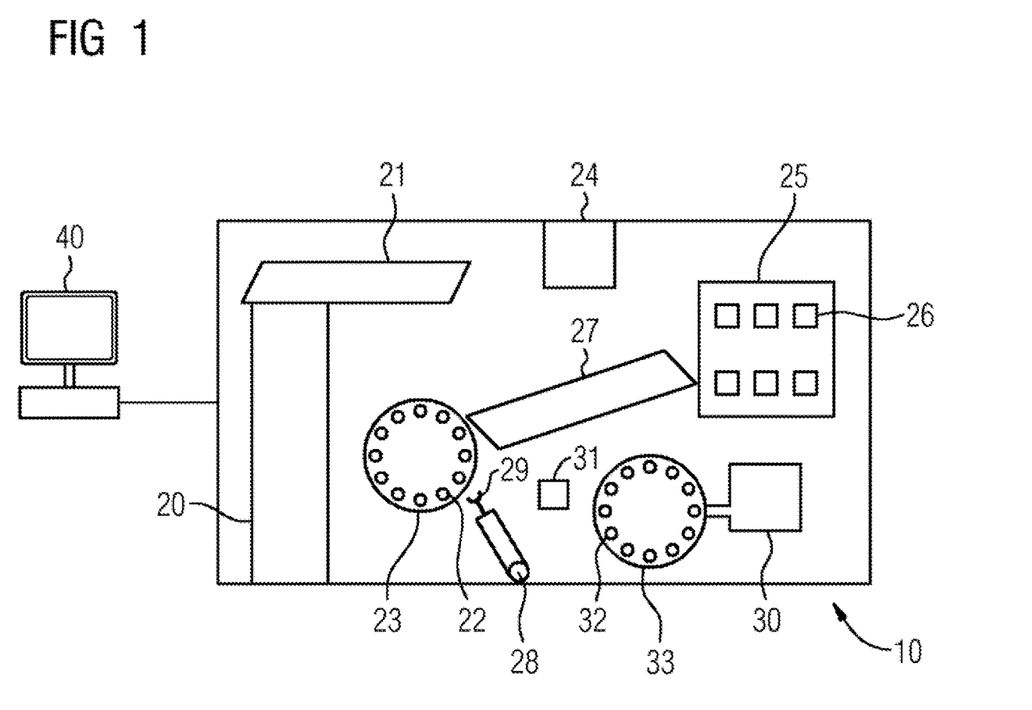
FIG. 1 shows an automatic analyzer according to the invention.

FIG. 1 is a schematic diagram of an automatic analyzer 10 with some components present therein. Here, only the most important components are shown, in highly simplified form, in order to illustrate the basic function of the automatic analyzer 10 without showing here the individual parts of each component in detail.

The automatic analyzer 10 is designed to carry out a very wide variety of different analyses of blood or other body fluids in a fully automated manner, without user activities being necessary therefor. On the contrary, necessary user interventions are limited to maintenance or repair work and refilling tasks, for example, when cuvettes need to be refilled or liquid containers need to be exchanged.

The patient samples are fed to the automatic analyzer 10 in primary sample vessels via a feed track 20 on carriages which are not shown in detail. Information regarding the analyses to be carried out for each sample can, for example, be transferred by means of barcodes affixed on the sample vessels, which barcodes are read in the automatic analyzer 10. Sample aliquots are removed from the sample vessels with the aid of a first pipetting device 21 by means of a pipetting needle.

The sample aliquots are fed to cuvettes, which are likewise not shown in detail and which are arranged in accommodation positions 22 of a rotatable incubation apparatus 23 adjusted in temperature to 37° C. The cuvettes are removed from a cuvette reservoir 24. Reagent vessels 26 containing various reagent fluids, such as, for example, a thrombin reagent fluid, are stored in the reagent vessel reservoir 25 cooled to about 8-10° C. Reagent fluid is removed from a reagent vessel 26 by means of the pipetting needle of a second pipetting device 27 and delivered to a cuvette already containing a sample aliquot, for example, a plasma sample, in order to provide a reaction mix. The cuvette containing the reaction mix is removed from an accommodation position 22 of the incubation apparatus 23 by the transfer arm 28 comprising a clamping gripper 29 and transferred to a shaking apparatus 31 in order to mix the reaction mix. After completion of the mixing process, the cuvette is further transported to an accommodation position 32 of the rotatable accommodation apparatus 33 for the photometric measurement station 30, where the absorbance of the reaction mix is measured.

The entire process is controlled by a central control unit 40, such as, for example, a computer connected via a data cable, assisted by a multiplicity of further electronic circuits and microprocessors within the automatic analyzer 10 and its components, which electronic circuits and microprocessors are not shown in detail.

The following example is to be considered illustrative of the invention, but not restrictive.

EXAMPLE

Performance of the Clauss Fibrinogen Method

One to 12.5 (1:12.5) dilutions of human plasma samples in the fibrinogen concentration range from about 1 g/L to about 5 g/L were produced in Owren's Veronal Buffer. One hundred μL of these diluted samples were adjusted to a temperature of +37° C., and 50 μL of temperature-adjusted thrombin reagent (about 100 IU/mL) were added. The reaction mixes were mixed, and the absorbance was measured photometrically with light of a wavelength of 405 nm over a period of about 80 seconds. The provision of the reaction mixes and the measurement of the absorbance were carried out in an automatic analyzer.

Reaction Kinetics Evaluation According to the Invention

The evaluation of the reaction kinetics, i.e., of the absorbance values measured over time, was done according to the invention, by ascertaining the maximum absorbance change of reaction kinetics by means of a regression method.

A calibration curve was prepared in the same way using plasma samples of known fibrinogen concentrations and using the associated maximum absorbance changes ascertained according to the invention.

Figure 2:
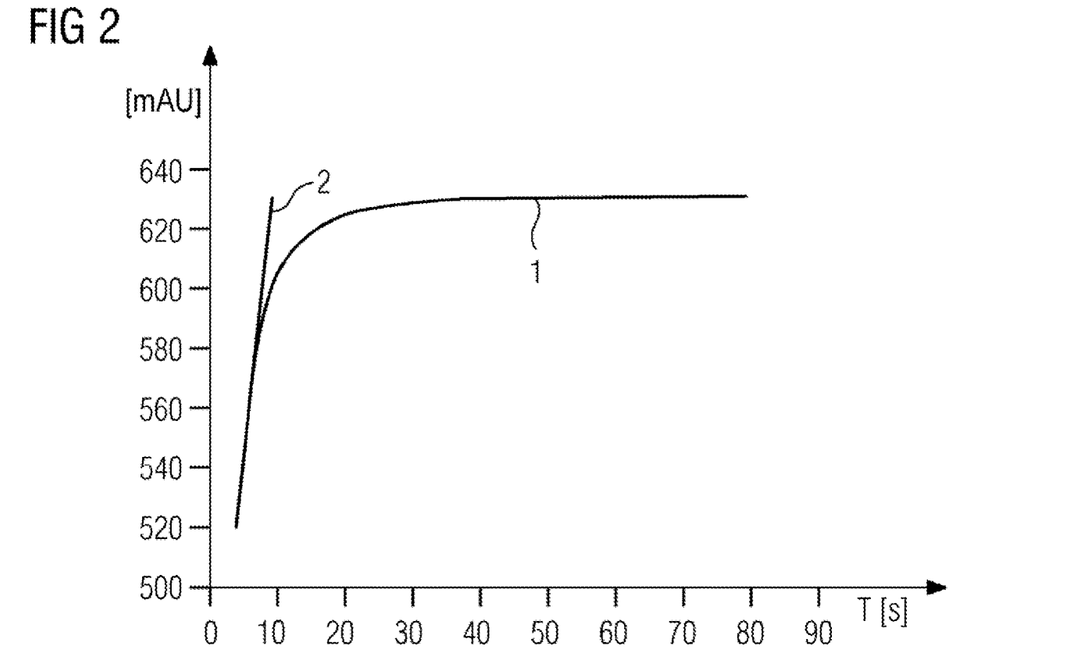
FIG. 2 shows reaction kinetics of a plasma sample of high fibrinogen concentration in the Clauss fibrinogen method.

FIG. 2 shows the time course of the absorbance values (mAU), i.e., the reaction kinetics (1), of a plasma sample of a high fibrinogen concentration (about 5 g/L). The reaction, i.e., the formation of fibrin, already started during insertion of the reaction vessel into the measurement channel (about 3-4 seconds after reagent addition). Here, it is already no longer possible to carry out exactly a traditional determination of the clotting time by means of the signal difference method, since the start signal is unknown. The determination according to the invention of the maximum reaction rate by means of an adapted regression interval is the method of choice here. Here, the adapted regression interval is very short (2 seconds). The straight line (2) is the straight line of the maximum reaction rate (absorbance change).

Figure 3:
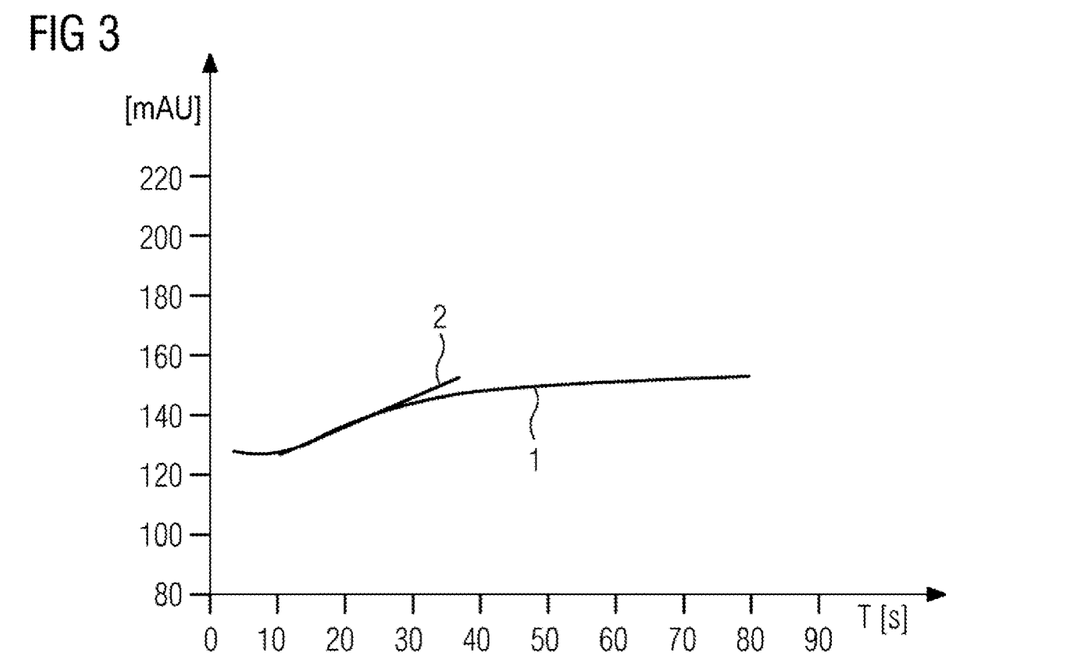
FIG. 3 shows reaction kinetics of a plasma sample of low fibrinogen concentration in the Clauss fibrinogen method.

FIG. 3 shows the time course of the absorbance values (mAU), i.e., the reaction kinetics (1), of a plasma sample of a low fibrinogen concentration (about 1 g/L). Here, the conversion of fibrinogen into fibrin occurs very slowly and sometimes without a clearly pronounced final plateau. In this case, the determination of the reaction rate is likewise the method of choice. Here, the adapted regression interval is extended (9 seconds). The straight line (2) is the straight line of the maximum reaction rate (absorbance change).

Figure 4:
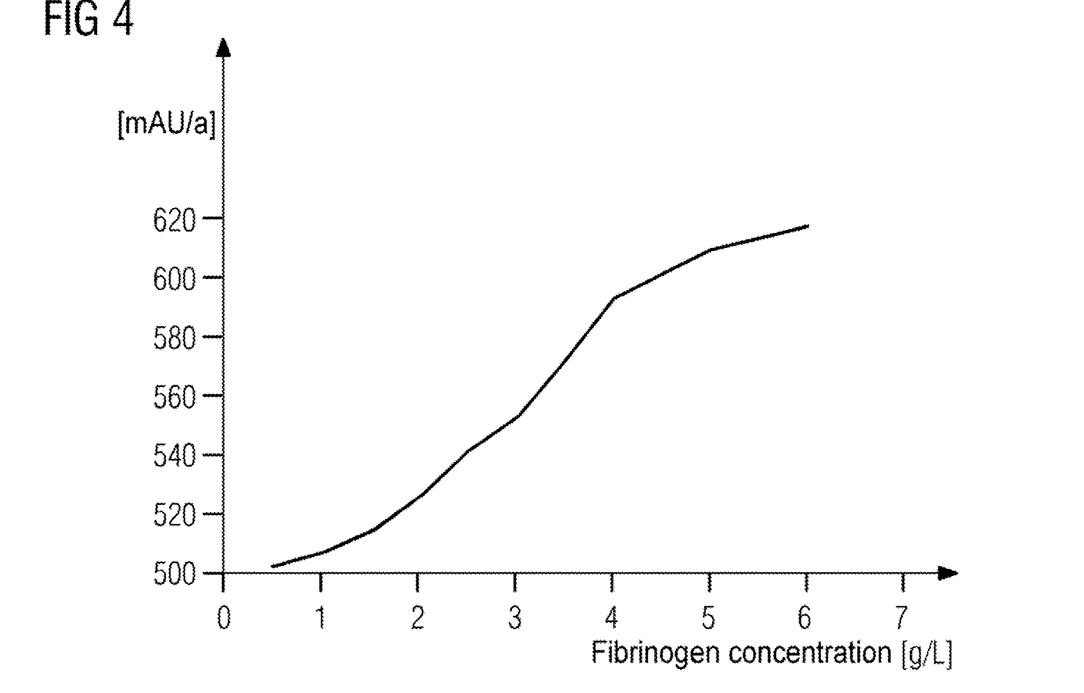
FIG. 4 shows a calibration curve according to the invention for the Clauss fibrinogen method.

FIG. 4 shows a calibration curve for the determination according to the invention of the concentration of fibrinogen. Ten plasma samples of known fibrinogen concentration between 0.5 and 6.0 g/L were analyzed using the method according to the invention and the maximum absorbance change [mAU/s] was determined in each case. In all intervals, there is a good spread among the data points. By means of a change in the sample dilution, for example as a 1:4.2 dilution of samples having a fibrinogen concentration of less than 1.0 g/L or a 1:25 dilution of samples having a fibrinogen concentration of more than 6.0 g/L, it would be possible to extend accordingly the measurable fibrinogen concentration range.

Figure 5:
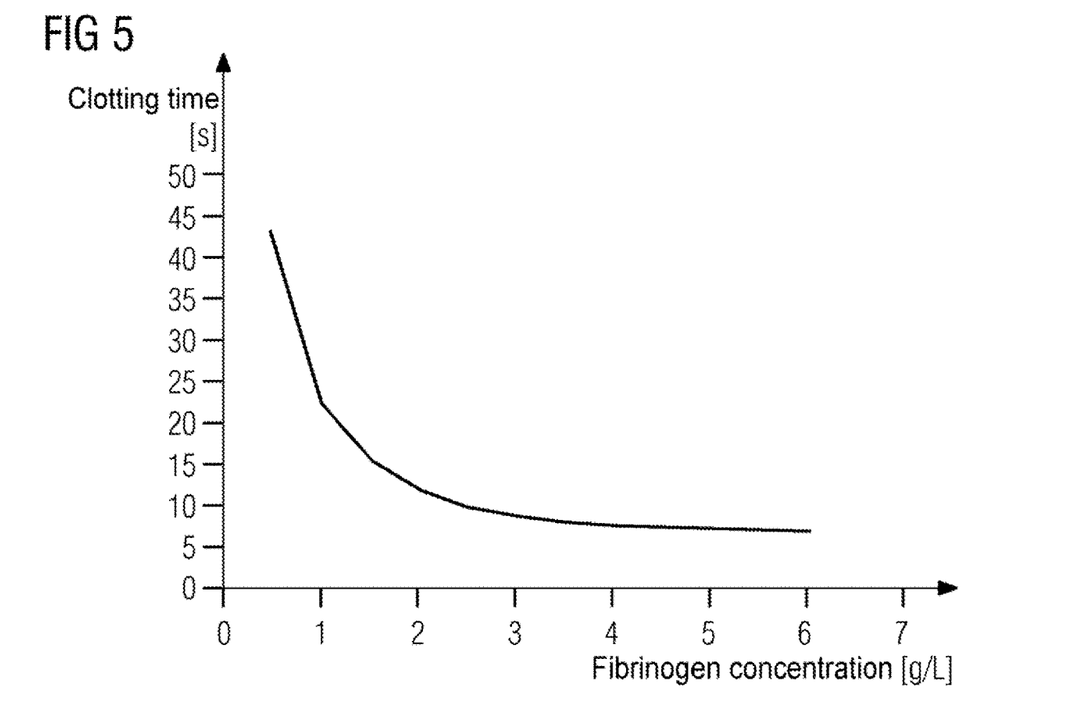
FIGS. 5 and 6 show calibration curves according to the prior art with clotting times for the Clauss fibrinogen method.
Figure 6:
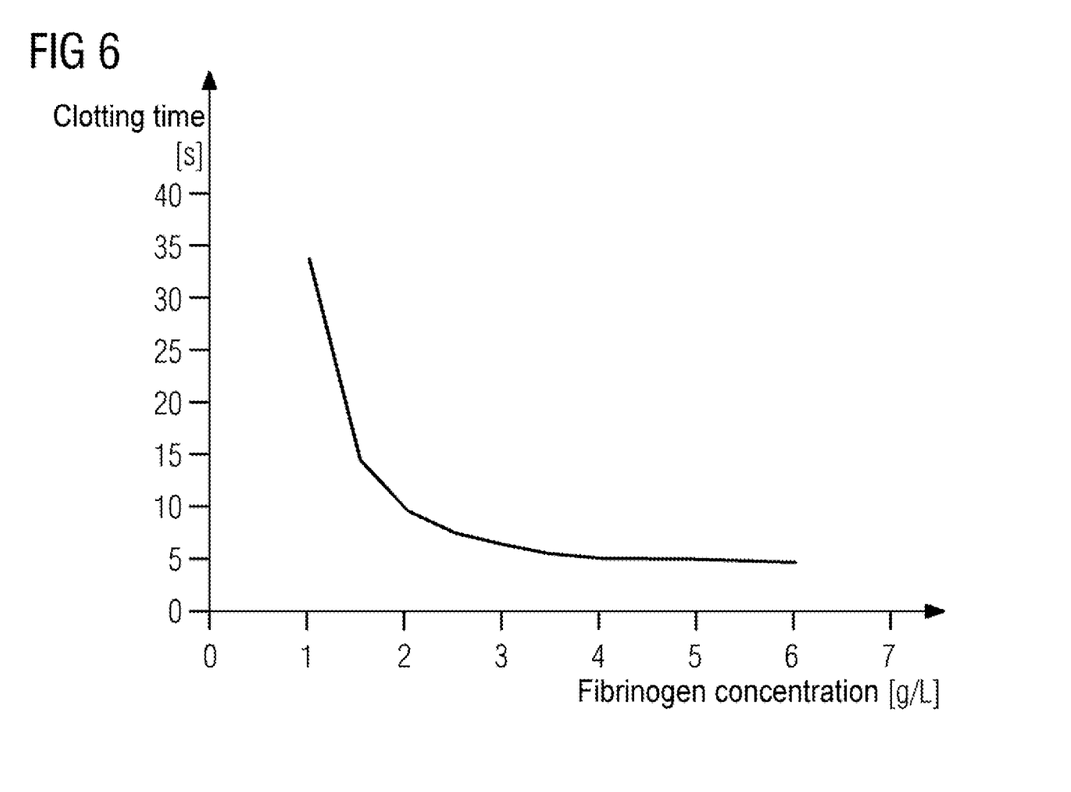

For comparison, FIGS. 5 and 6 show calibration curves for the hitherto customary Clauss fibrinogen determination methods with an evaluation of the clotting time via thresholds (FIG. 5) or via the percentage signal difference (FIG. 6). In both cases, the profile of the calibration curve above about 4 g/L is already so flat that a meaningful evaluation of the raw values is practically no longer possible. Thus, samples having a fibrinogen concentration of more than 4 g/L would already have to be diluted more strongly and measured again. The reason for the strong flattening is, inter alia, the already started reaction at the time of recording of the first measurement value.

Furthermore, an evaluation of clotting times determined using the threshold method is not possible at a concentration of 0.5 g/L, since the signal does not reach the minimum threshold. A reduction of the threshold as a possible solution entails the risk of false evaluations owing to overlays in the reaction curve (e.g., by air bubbles).

LIST OF REFERENCE SIGNS

1 reaction kinetics
2 straight line
10 analyzer
20 feed track
21 pipetting device
22 accommodation position
23 incubation apparatus
24 cuvette reservoir
25 reagent vessel reservoir
26 reagent vessel
27 pipetting device
28 transfer arm
29 clamping gripper
30 measurement station
31 shaking apparatus
32 accommodation position
33 accommodation device
40 control unit

The invention claimed is:

1. A method for determining a concentration of fibrinogen in a plasma sample according to the Clauss method, the method for determining the concentration of fibrinogen comprising:
adding thrombin to the plasma sample to provide a reaction mixture containing the plasma sample and the thrombin,
measuring absorbance values of the reaction mixture over time, wherein start of the measuring occurs after a period of time from the adding the thrombin to the plasma sample,
preparing a reaction curve from the measured absorbance values over time,
ascertaining a maximum absorbance change by using a regression method, and
determining the concentration of fibrinogen with the aid of a calibration curve prepared from an assignment of known fibrinogen concentrations and maximum absorbance changes.

2. The method as claimed in claim 1, wherein the regression method comprises:
determining a first, provisional maximum absorbance change in the reaction curve using a predetermined first regression interval,
determining a second regression interval on the basis of the first, provisional maximum absorbance change and on the basis of predetermined parameters, and
determining the maximum absorbance change using the second regression interval.

3. The method as claimed in claim 1, wherein the period of time ranges from 0.5 to 5 seconds between the adding the thrombin to the plasma sample and the start of the measuring of the absorbance values of the reaction mixture.

4. The method as claimed in claim 3, wherein the period of time between the time of adding the thrombin to the plasma sample and the start of the measuring of the absorbance values of the reaction mixture is from 3 to 4 seconds.

5. An automatic analyzer comprising at least one pipetting device, a photometric or nephelometric measurement station and a data processing unit, wherein the analyzer further comprises a controller configured to control a method for determining a concentration of fibrinogen in a plasma sample according to the Clauss method, the method for determining the concentration of fibrinogen comprising:
adding thrombin to the plasma sample to provide a reaction mixture containing the plasma sample and the thrombin,
measuring absorbance values of the reaction mixture over time, wherein start of the measuring occurs after a period of time from the adding the thrombin to the plasma sample,
preparing a reaction curve from the measured absorbance values over time,
ascertaining a maximum absorbance change by using a regression method, and
determining the concentration of fibrinogen with the aid of a calibration curve prepared from an assignment of known fibrinogen concentrations and maximum absorbance changes.

6. The automatic analyzer as claimed in claim 5, further comprising a first accommodation position for reaction vessels at which the providing of the reaction mixture occurs, and a second accommodation position for reaction vessels located at the measurement station, and a device for transporting a reaction vessel from the first accommodation position to the second accommodation position, wherein the controller is further configured to control the following:
providing in the first accommodation position a reaction vessel containing the reaction mixture by adding thrombin to a plasma sample present in the reaction vessel,
transporting the reaction vessel from the first accommodation position to the second accommodation position, and then
measuring absorbance values of the reaction mixture over time in the measurement station,
wherein the period of time ranges from 0.5 to 5 seconds between the adding the thrombin to the plasma sample and the start of the measurement of the absorbance values of the reaction mixture.

7. The automatic analyzer as claimed in claim 4, wherein the period of time between the time of adding the thrombin to the plasma sample and the start of the measuring of the absorbance values of the reaction mixture is from 3 to 4 seconds.

* * * * *